United States Patent [19]
Gallant

[11] Patent Number: 5,350,299
[45] Date of Patent: * Sep. 27, 1994

[54] DENTAL TREATMENT SYSTEM
[75] Inventor: Ben J. Gallant, Corpus Christi, Tex.
[73] Assignee: American Dental Technologies, Inc., Troy, Mich.
[ * ] Notice: The portion of the term of this patent subsequent to Jul. 19, 2011 has been disclaimed.
[21] Appl. No.: 29,732
[22] Filed: Mar. 25, 1993

Related U.S. Application Data
[63] Continuation-in-part of Ser. No. 859,158, Mar. 27, 1992.

[51] Int. Cl.$^5$ .............................................. A61C 3/02
[52] U.S. Cl. .................................... 433/88; 451/75
[58] Field of Search ................ 433/88; 51/410, 438

[56] References Cited

U.S. PATENT DOCUMENTS

| | | | |
|---|---|---|---|
| 2,661,537 | 12/1953 | Angell | 433/88 |
| 2,696,049 | 12/1954 | Black | 433/88 |
| 3,971,375 | 7/1976 | Hill | 128/173.1 |
| 4,276,023 | 6/1981 | Phillips et al. | 433/85 |
| 4,492,575 | 1/1985 | Mabille | 433/88 |
| 4,494,932 | 1/1985 | Rzewinski | 433/88 |
| 4,635,897 | 1/1987 | Gallant | 251/5 |
| 4,708,534 | 11/1987 | Gallant | 406/7 |
| 4,767,404 | 8/1988 | Renton | 604/48 |
| 4,826,431 | 5/1989 | Fujimura et al. | 433/29 |
| 4,893,440 | 1/1990 | Gallant et al. | 51/436 |
| 4,940,411 | 7/1990 | Vassiliadis | 433/215 |
| 5,055,048 | 10/1991 | Vassiliadis | 433/215 |
| 5,205,743 | 4/1993 | Ludvigsson et al. | 433/92 |

Primary Examiner—John J. Wilson
Attorney, Agent, or Firm—Synnestvedt & Lechner

[57] ABSTRACT

A system of treating teeth or associated tooth structure using an abrasive-laden fluid stream provides fluid at high pressure to a manifold with selectively operable valves to deliver fluid at a selected pressure to a mixer for the fluid and abrasive and delivery to a device for application to a patient's mouth. Priming air at low pressure pressurizes the mixer. An alternate air path bypasses the mixer. A selective control delivers a stream of fluid or fluid and abrasive to the tooth or tooth structure. Upon termination of treatment, pure air is diverted through a purge line to purge the system of abrasive. A vacuum is selectively operable to remove abrasive and debris from the mouth during and after the abrasive treatment. The abrasive delivery device includes a hand-held nozzle having ports operable by the fingers for control. The vacuum includes a rigid, disposable collection chamber for sterile disposal of the abrasive and debris and has a common filter for the purge circuit and for removal of abrasive and debris from the mouth. Connection to the dental office suction system or a water powered venturi provides suction. Pressure regulation and relief insures instantaneous change from one pressure level to the next.

14 Claims, 7 Drawing Sheets

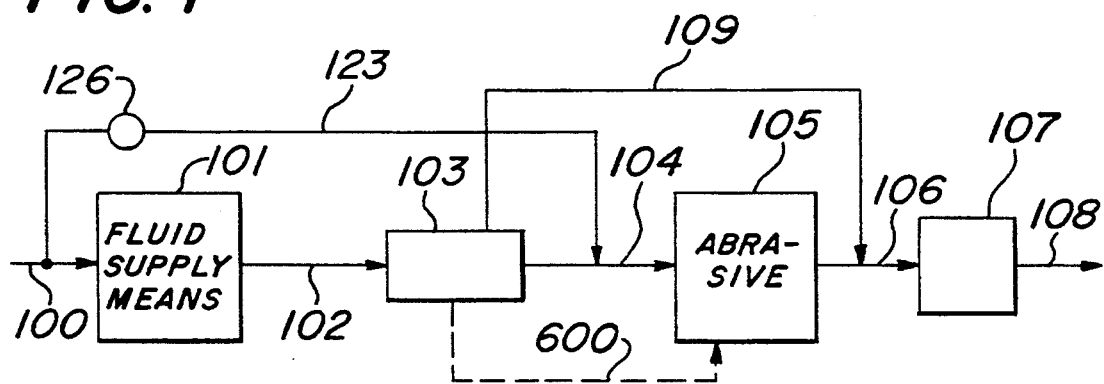
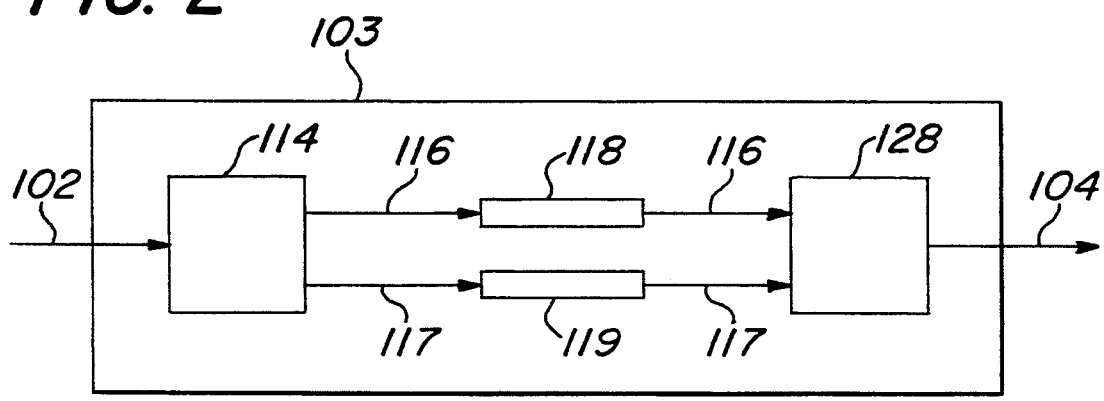
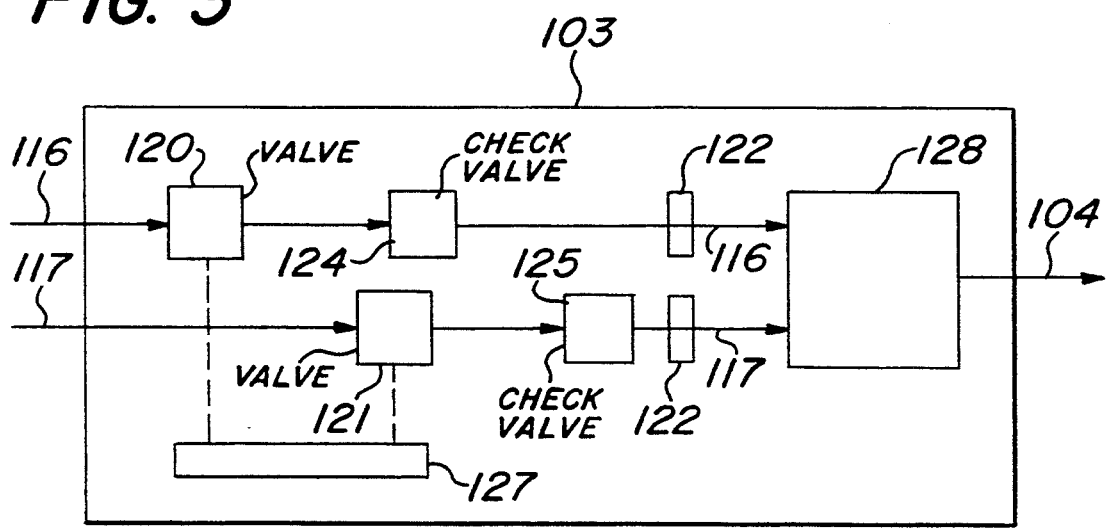

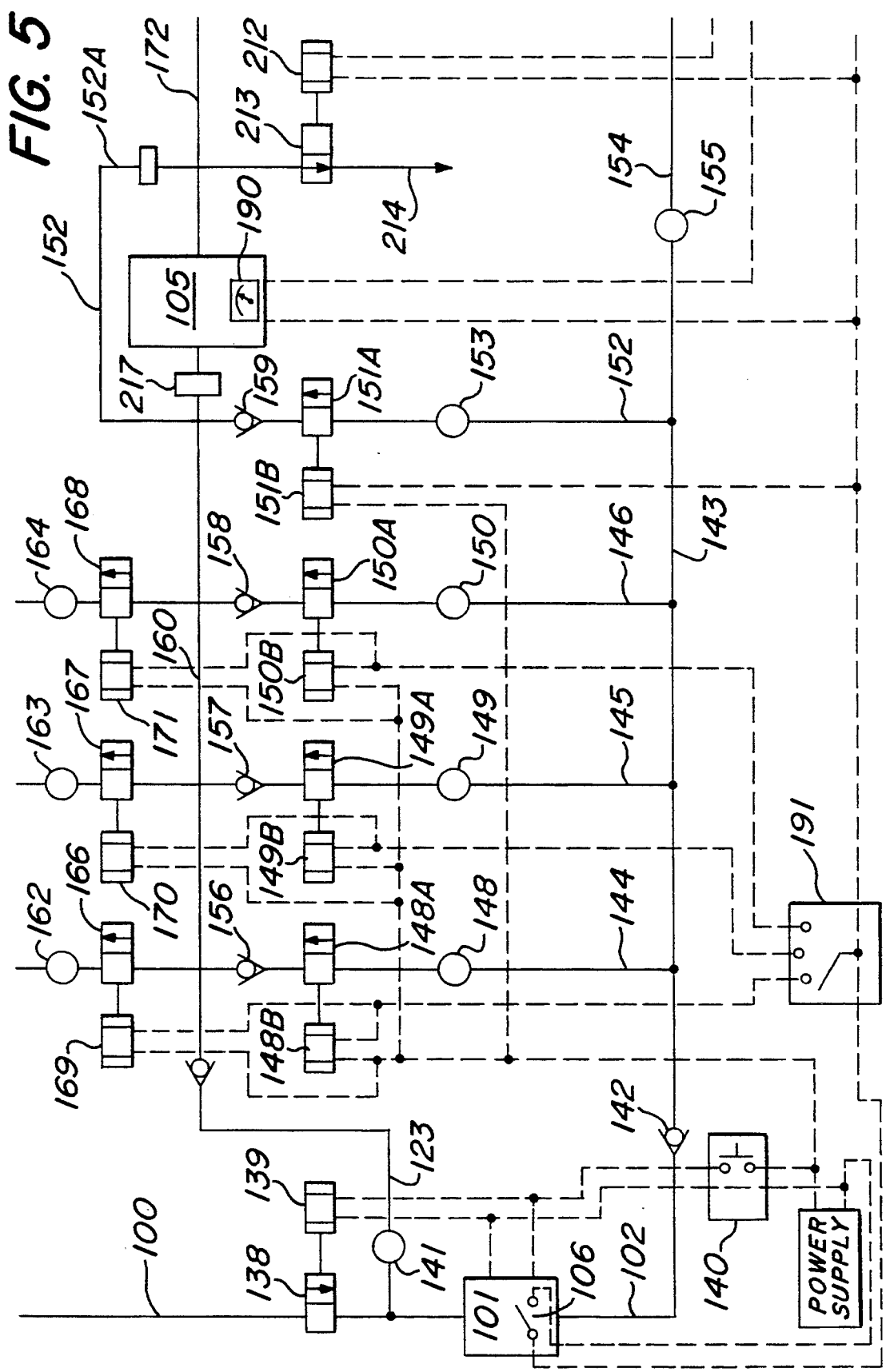

DENTAL TREATMENT SYSTEM

RELATED APPLICATION

This application is a continuation-in-part of copending application Ser. No. 07/859,158, filed Mar. 27, 1992.

FIELD OF THE INVENTION

The present invention relates to systems used in the practice of dentistry, and more particularly, to systems for cutting, excavating and etching teeth or associated tooth structure by means of finely divided abrasive materials carried in a fluid stream.

BACKGROUND OF THE INVENTION

The use of abrasive-laden fluid streams to treat teeth has long been known. For example, U.S. Pat. No. 2,661,537 to Angell describes equipment for treating teeth with a relatively high-pressure stream laden with abrasive particles. While the use of such equipment has gained a significant degree of success in connection with the cleaning of teeth, there has heretofore been an overall lack of success in the dental industry with respect to the use of such equipment for cutting, excavating or etching teeth. Applicant has found that this lack of success can be attributed to several heretofore unrecognized disadvantages associated with equipment of the type described in Angell.

For example, cutting or etching of teeth with gas/abrasive streams frequently requires a source of fluid at pressures of at least about 120 psig. Unfortunately, however, compressed air in the range of about 60 to 80 psig is generally the highest pressure available in dental operatories. In order to overcome this limitation, the Angell patent describes the use cylinders containing $CO_2$ gas at a pressure of about 800 psig as a source of pressurized fluid. Applicant has found that there are numerous disadvantages associated with the use of pressurized gas in this form. For example, applicant has found that one important factor in successfully achieving cutting, etching and/or excavating tooth enamel is proper regulation and control of the pressure at which such operations are carried out. Such precise control and regulation is difficult to achieve in the system described in Angel. One reason for this difficulty is the very large pressure differentials between the pressure needed to operate the system (e.g. 100 to 120 psig) and the pressure at which the gas is delivered (800 psig). In particular, the accuracy of pressure regulation equipment is frequently inversely proportional to the pressure differential across the regulating device. Thus, the precision of the regulated pressure frequently decreases as the pressure differential increases.

Another disadvantage of the equipment described in Angell is that it is capable of providing only two pressure levels for the fluid utilized to operate the system. Applicant has found that this is another reason for the lack of success achieved by prior devices. It is highly desirable to operate at more than two distinct and different pressure levels because of the multiplicity of dental procedures performed by the dentist. The equipment described in Angell, however, is capable of supplying fluid at only two distinct pressure levels. As a result, the required precision in operating the dental instrument is deficient. Another disadvantage arises on account of the provision for the supply of gas in compressed form in cylinders. In view of the considerable volume of gas being used, cylinder replacement becomes a severe inconvenience. Thus, applicant has found that the use of equipment as described in Angell is a disadvantage in treatment operations involving the use of abrasive-laden fluid streams.

The prior art use of abrasive-laden fluid streams for treatment of teeth has also suffered from the disadvantageous of having significant excess and/or post-use abrasive particles in the area of the mouth during operation. The presence of such abrasive particles is not only uncomfortable to the patient being treated, but it may also constitute a hinderance to the dentist conducting the operation. This disadvantage is particularly relevant for cutting and abrading of teeth since the relatively high pressures required for such operations sometimes result in a cloud or mist of excess or post-use abrasive particles which make it difficult for the dentist to see the area being treated. This difficulty has heretofore not been fully overcome.

OBJECTS AND SUMMARY OF THE INVENTION

In view of the deficiencies of the prior art, it is thus an object of the present invention to provide improved dental systems which utilize pressurized fluid streams containing abrasive particles for effectively and efficiently abrading, etching and cutting teeth or associated tooth structure. As used herein, by associated tooth structure is meant fillings, composites, facings, crowns, caps, amalgam and the like.

It is a further object of the invention to bring together the components needed to produce a novel and effective dental tool capable of overcoming past deficiencies of systems using abrasive-laden fluid streams.

It is a further object of this invention to provide dental apparatus for treating teeth via an abrasive-laden stream of high pressure fluid, such as air, in which the disadvantages associated with the presence of excess abrasive particles are eliminated or substantially reduced.

It is a further object of the present invention to provide dental apparatus which utilize pressurized fluid streams containing abrasive particles wherein the apparatus is capable of operating selectively at two or more precisely controlled pressure levels.

Yet another object of the invention is the use of a common suction system for purging the equipment of excess abrasive particles and collection of post-use abrasive particles. The common suction system may include connection means for connection to the office suction and waste collection systems pre-existing within the dental office. Advantageously, suction may be provided by a water venturi which draws off abrasive particles and debris into the water stream passing through the venturi.

These and other objects are satisfied by the preferred system aspects of the present invention. The present system is directed to the treatment of teeth by means of abrasive particles carried by a gas stream. According to one preferred embodiment, the system comprises, in combination with a source of air: means for increasing the pressure of said air to an initial pressure; a pressure selection means for selectively providing said air at least a first or a second pressure, each of said first and second pressures being less than about said initial pressure; an abrasive delivery means for combining the abrasive particles with said air at one of said first or second pressures to provide an abrasive-laden air stream; and nozzle means for delivering said abrasive-laden air stream to the teeth to be treated. According to another preferred embodiment, the system comprises, in combination with a source of air at an initial pressure: a pressure selection means for selectively providing said fluid at least a first, a second, or a third pressure, each of said first, second and third pressures being less than about said initial pressure; an abrasive delivery means for combining finely divided abrasive particles with said air at one of said pressures to provide an abrasive-laden air stream; and nozzle means for delivering said abrasive-laden air stream to the teeth to be treated.

Another aspect of the present invention, which is preferably used in combination with the treatment system aspects hereof, is directed to evacuation systems especially well adapted for removing excess and/or post-use abrasive particles from in and around the area of the mouth during dental operations- Such systems preferably comprise a vacuum conduit having a first, relatively large diameter outer conduit member and a second, relatively small diameter inner conduit member, wherein said first and second members are moveable in a longitudinal direction with respect to one another. In this configuration, the outer conduit member may be placed adjacent to the chin, cheek, or lips of the patient receiving treatment while the inner conduit member may be selectively positioned within the mouth of the patient being treated.

The evacuation system may include integral vacuum means and may optionally and additionally include means for connection to the dental office suction system for the evacuation of particulate debris and abrasive.

Another aspect of the present invention, which is optionally but not necessarily used in combination with one or more of the other aspects hereof, is directed to a system for controlling the pressure of the abrasive/air mixture leaving the delivery nozzle means. Such control systems preferably include pneumatic control means, such as fluid discharge ports on the handle of the dental apparatus for activating or deactivating the flow of pressurized fluid therein.

BRIEF DESCRIPTION OF THE DRAWINGS

FIG. 1 is a block diagram showing the elements of one embodiment of the delivery system of the present invention.

FIG. 2 is a block diagram showing one embodiment of the pressure selector means 11 illustrated in FIG. 1.

FIG. 3 is a block diagram showing one embodiment of one aspect of the pressure selector means shown in FIG. 2.

FIGS. 5 and 5A are block diagrams showing a preferred embodiment of the treatment systems of the present invention, including the control systems therefor.

DETAILED DESCRIPTION OF PREFERRED EMBODIMENTS

Figure 4:
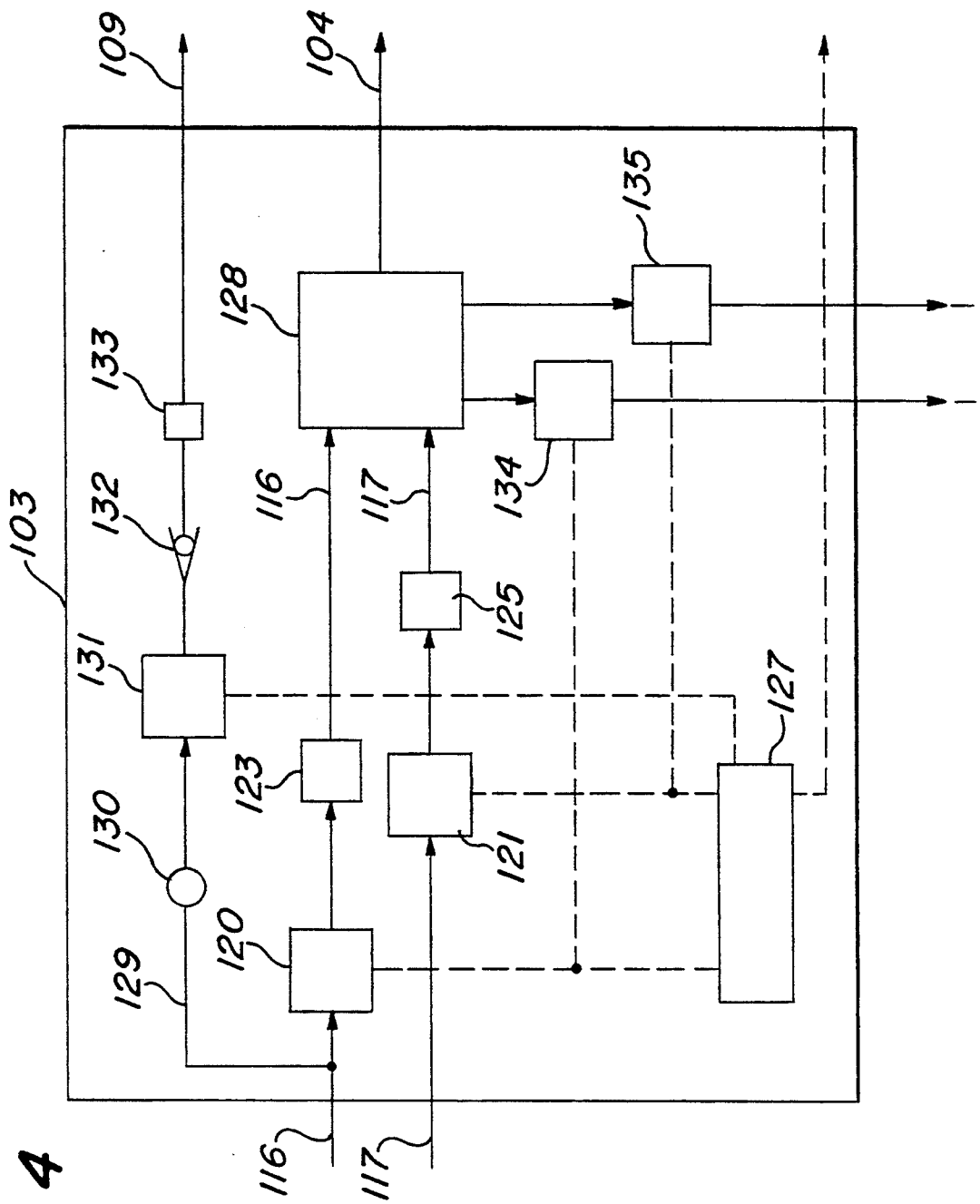
FIG. 4 is a block diagram showing a second embodiment of one aspect of the pressure selecting means illustrated in FIG. 2.

The present invention is directed generally to dental treatment systems and dental components adapted for use in connection with such systems. As the term is used herein, "treatment" refers to any operation for altering the physical condition of the teeth or gums by impacting same with an abrasive-laden fluid stream. As the term is used herein, "teeth" refers to teeth in their natural state as well as teeth that have been filled or otherwise modified by earlier dental treatment.

FIG. 1 is a schematic representation of a system embodying the present invention and utilizing a stream of operating fluid delivered through a conduit 100. The illustrated system comprises the following components: fluid supply means 101 connected to the conduit 100 for providing a stream of said fluid in a second conduit 102 at an initial pressure; pressure selection means 103 connected to the stream within conduit 102 for selectively providing a fluid stream within a conduit 104 at least at a first or second pressure, each of said pressures being less than about the initial pressure of the stream in conduit 102; means 105 connected to conduit 104 for combining said fluid stream within conduit 104 with abrasive particles to produce an abrasive-laden fluid stream within a delivery conduit 106; and handpiece means 107 connected to conduit 106 for discharging or delivering a stream or fluid jet 108 against the tooth or tooth structure of the patient to be treated.

Preferably, pressure selection means 103 also comprises means for selectively providing a substantially abrasive-free stream of pressurized fluid to said handpiece means 107 by means of a conduit 109. Thus, preferred systems of the type disclosed in FIG. 1 may alternatively and selectively be operated in a first mode wherein the abrasive-laden stream is provided to handpiece means 107 or a second mode wherein a substantially abrasive-free stream is provided to the handpiece. Applicant has discovered that highly desirable and beneficial characteristics are associated with dental treatment systems having such a pressure selection means. For example, the systems of the present invention are designed to provide abrasive-laden fluid streams for cutting of teeth, such as is required in preparation for filling of cavities with amalgam or the like. As the cavity is expanded by the abrasive-laden stream, the abrasive particles may sometimes tend to settle or collect in the cavity and produce a layer of abrasive particles in the cavity. The presence of this layer, in turn, may reduce the effectiveness of the cutting operation under certain conditions. Accordingly, it is a highly desirable aspect of the present invention that the dental treatment system of the present type be selectively operable between an abrasive-laden mode and an abrasive-free mode so that such layer can be readily removed by blowing with a stream of air. It has been found that the use of abrasive-free air acts to dry the tooth undergoing treatment which allows for better cutting and abrading efficiency.

As described above, an important consideration in achieving successful operation of dental treatment systems is the degree to which the system permits precise control and regulation of the fluid operating pressure. This consideration is important because the regulation of fluid pressure helps to control the action of the abrasive-laden stream on the tooth. However, the rate at which abrasive particles are delivered to the fluid stream is also frequently an important variable in achieving successful system operation. That is, fluid pressure and abrasive delivery rate each have an influence upon the cutting or abrading characteristics of the fluid stream. Moreover, it has been discovered that a specific correspondence or relationship between fluid pressure and abrasive delivery rate should exist in order to achieve results which are consistently commercially acceptable. Improper matching of these two operating parameters can preclude effective operation of the dental system. The pressure selection means 103 of the present invention preferably includes means for providing a control signal 110 for controlling the rate at which abrasive delivery means 105 provides abrasive to the fluid stream within conduit 104. The present system preferably operates such that the control signal 110 be modulated according to the pressure selected. In this way, the systems of the present invention are capable of producing an abrasive delivery rate which is precisely matched to the pressure selected and hence to the desired operation. In general, it can be said that at relatively low pressures, abrasive powder tends to accumulate at relatively low points in the system, whereas by moving air at a faster rate, higher pressures above a given pressure, depending upon the design of the systems, will be effective to move all of the powder available.

The present system optionally includes means 112 (illustrated in FIGS. 6 and 7) in juxtaposition to the mouth of the person being treated for removing excess and/or post-use abrasive particles from in and around the mouth.

The present systems also optionally may include or are associated with a dental laser of the type described, for example, in U.S. Pat. Nos. 5,055,048, issued Oct. 8, 1991 and 4,940,411, issued Jul. 10, 1990. According to such preferred embodiments, the present treatment systems further include means for directing a beam of laser light toward the teeth of the patient being treated. In this way, the dentist or other dental professional may utilize the present system to alternatively and selectively treat the teeth of the patient with an abrasive-laden fluid stream or a dental laser.

The components of the present systems may be housed, either together or separately, in one or more suitable housings. In certain embodiments, however, it is preferred that the dental treatment systems be incorporated into a stand-alone, portable unit which can be transported to numerous locations and connected to the appropriate local power supply and fluid source. In such embodiments, it is preferred that the components are housed together on or in a relatively compact housing.

A. Fluid Supply Means

The nature and character of the fluid supply means 101 of the present invention may vary widely, depending upon numerous factors, such as the particular operating fluid being used. The material which comprises the fluid stream supplied through conduit 100 may also vary widely within the scope hereof, depending upon such factors as cost and availability, and the use of a wide variety of materials are within the scope hereof. It is preferred, however, that the fluid of the present invention comprise a gaseous material, and even more preferably air.

It will be also appreciated that the construction of fluid supply means 101 may vary depending upon factors such as the pressure of the operating fluid being used. For example, it is contemplated that in certain embodiments the fluid source within conduit 100 is provided at a pressure which is sufficiently high to operate the dental systems of the present invention without further compression. In such embodiments, the fluid supply means 101 may simply comprise, for example, a supply conduit for transporting the fluid from its source to the pressure selection means 103. As mentioned above, however, the preferred fluid, i.e., air, is generally only available in dental operatories at pressures limited to about 60 to at most about 90 psig. This source of operating fluid is preferred because of its ready availability and low cost. While air at such pressures may be acceptable for numerous dental applications, applicant has found that such pressures are insufficient to perform the preferred etching and cutting operations for which the present system is especially well adapted. In particular, applicant has found that successful cutting, abrading and etching operations require a source of gas at a pressure of from about 80 to 200 psig. According to preferred embodiments, therefore, the preferred fluid source comprises operatory air at a pressure of less than about 80 to about 90 psig and the fluid supply means 101 comprises means for increasing the pressure of the operatory air to greater than about 80 psig, and even more preferably to a pressure of from about 80 to about 200 psig.

The pressure increasing means of the present invention may comprise any one of several well known structures for increasing the pressure of the selected fluid medium. The selection of any particular pressure increasing means will depend upon numerous factors such as flow rate, pressure differentials, sealing methods, methods of lubrication, power consumption, serviceability and cost. It is contemplated, therefore, that the pressure increasing means may take numerous forms within the scope hereof. For embodiments in which the operating fluid is a gas, it is contemplated that the pressure increasing means may comprise, for example: fans, both axial and centrifugal; compressors, both axial and centrifugal; rotary blowers; reciprocating compressors, both single stage and two stage; and ejectors. For embodiments in which the preferred fluid is air, the preferred means for increasing the fluid pressure comprises an air pressure intensifier of the type sold, for example, by Haskel Incorporated of Burbank, Calif. 97502, under Model No. MAA-2.5.

The fluid supply means 101 according to preferred embodiments also includes means for storing the pressurized fluid. The fluid supply means 101 also preferably includes means for stabilizing the pressure of fluid stream within conduit 102. According to simple and effective embodiments of the present invention, the means for storing the pressurized fluid also acts as the means for stabilizing the pressure of fluid stream 102. For example, the air exiting the pressure increasing means in the preferred embodiment is transported to a fluid supply tank adapted to maintain a reservoir of the pressurized air. This fluid supply tank not only provides a high pressure reservoir, it also serves to buffer or dampen the pressure spikes or fluctuations frequently encountered with dental operatory air. For preferred embodiments, especially those in which the present system is a substantially portable system, the fluid supply tank comprises an air storage bottle capable of maintaining at least one cubic feet of air at a pressure of about 250 psi. In this way, fluctuations in the pressure of the fluid exiting the fluid supply means is minimized.

B. Means For Selectively Reducing the Fluid Pressure

With reference to FIG. 2, an important aspect of the present dental treatment systems resides in the provision of means 103 for selectively reducing the pressure of the fluid stream within conduit 102. In particular, means 103 makes the operating fluid selectively available at least at two and preferably at least three discrete pressure levels, said discrete pressure levels each preferably being less than about the initial pressure level of the fluid provided by the fluid supply means 101 but substantially above atmospheric. While it is contemplated that numerous structures may be adaptable for use as the pressure selection means, it is preferred that the pressure selection means 103 comprise inlet manifold means 114 connected to said fluid supply means 101 for providing at least first and second flow paths 116 and 117 for the operating fluid. Each of said first and second flow paths 116 and 117 preferably include pressure regulating means 118 and 119 for precisely regulating the pressure in a downstream portion of the flow path. Unless the context clearly indicates otherwise, the term "downstream" refers to that region of the flow path downstream of the pressure regulating means and "upstream" refers to that region of the flow path upstream of the pressure regulating means. Each flow path is thus divided by its respective pressure regulating means into a high pressure upstream portion and a low pressure downstream portion. According to highly preferred embodiments, the flow paths are connected in parallel configuration. That is, the manifold means 114 is configured such that the upstream pressure in said first flow path 116 is substantially equivalent to about the upstream pressure in said second flow path 117.

The preferred selective pressure reduction means 103 is readily adaptable and well suited for selectively providing the operating fluid at three or more pressure levels, with each of said pressure levels being less than about the initial pressure of the fluid provided by the fluid supply means. Applicant has found that such an embodiment is especially beneficial for the provision of a dental treatment system well adapted for use in each of the following three dental operations: cutting, etching and abrading. Thus, it is highly preferred that the inlet manifold means 114 include means for providing a first flow path, a second flow path and a third flow path, each of said flow paths being connected in a parallel configuration. The use of such a configuration according to the preferred aspects of the present invention permits the utilization of three distinct, precisely controllable operating pressures for the dental instrument. Applicant has found that this is an important feature of such preferred embodiments since it allows flexibility of use while simultaneously preserving precise control and regulation of the necessary fluid stream. For use in applications where the cleaning of the teeth is contemplated, a fourth parallel flow path may be provided with pressure in the fourth flow path being regulated to a level which is lower than the other pressure levels.

With particular reference now to FIG. 3, the selective pressure reduction means 103 of the present invention also preferably includes selective valve means 120 and 121 in a portion, and preferably a downstream portion, of each of the flow paths 116 and 117 for selectively blocking and unblocking the flow of fluid through the respective flow paths. It is contemplated that numerous valves of the type known and available in the industry are adaptable for use for this purpose, and all such valves are within the scope of the present invention. According to preferred embodiments hereof, as disclosed more fully hereinafter, the valves of the present invention are preferably high pressure solenoid operated valves of a type well known in the art. Each of the flow paths also preferably includes in a downstream portion thereof, means 124 and 125 for preventing back flow of said pressurized fluid. The back-flow prevention means are preferably located in a portion of said flow path which is downstream of said valve means 120 and 121. In a typical arrangement, means 124 and 125 each comprise a check valve in the flow path immediately downstream of valve means 120 and 121, respectively, each such check valve being of any type and construction well known in the art. Additionally, a filters 122 for removing unwanted debris or particles from the fluid should be included in a downstream portion of the flow paths. The filters are of particular importance in the prevention of the migration of abrasive back into the solenoid operated valves and the check valves, thus avoiding equipment failure.

Another aspect of the invention illustrated in FIG. 1 involves the supply of gas at a pressure close to but somewhat below the lower of any of the operating pressures established by the selective pressure reduction means, directly to the inlet of the abrasive particle delivery system. For reasons which will become apparent in the following, it is of importance that at start up, prior to the selection of any particular operating pressure level, the abrasive particle delivery system be immediately activated by the supply of regulated air under pressure. For this purpose, in systems where operatory air at pressures of about 80 psig is available in conduit 100, a branch conduit 123 delivers regulated air directly from line 100 to air/abrasive unit 105. In order to regulate the pressure of this air supply, a pressure regulator 126 is provided which maintains the pressure in line 123 at a preset limit, for example, between about 60 and about 80 psig.

The selective pressure reducing means 103 preferably comprises control means 127 for providing a control signal (indicated by dashed lines) to the valve means 120 and 121, thereby selectively opening and/or closing the valve means. In the preferred embodiments in which the valve means is a solenoid operated valve, the control means comprises a solenoid for each of said valves and an electrically operated circuit for opening and closing the solenoid valve, as more fully described hereinafter.

The pressure reducing means 103 also preferably includes an exit manifold means 128 connected to flow paths 116 and 117. The function of the exit manifold means 28 is to provide a source of fluid 104 at the selected pressure to the air/abrasive means 105. Thus, the exit manifold means 128 preferably comprises a conduit connected between a downstream portion of each of said flow paths 116 and 117 and said abrasive delivery means.

The selective pressure reduction means 103 also preferably includes pressure relief means for relieving fluid pressure in excess of that selected for the particular operation. Important functions of the pressure relief means are to ensure that pressure of the fluid is immediately adjusted to the selected pressure and, in addition, that it does not unexpectedly and unwantedly rise, because of a malfunction in the system, substantially beyond that pressure selected by the dentist or other dental professional. Control means is also preferably provided for selectively controlling the relief means such that the activating pressure of the relief means corresponds to or is slightly greater than the maximum pressure in the pressure range selected by the dentists. As the term is used herein, "activating pressure" refers to the pressure at which the pressure relief system relieves the build-up of pressure in the system.

It will be appreciated that the provision of such pressure relief means according to the present invention constitutes an important aspect of certain embodiments hereof. For example, the relief means provides a way of immediately establishing a selected pressure and gives the health professional a confidence that the desired pressure level is reliably at the pressure selected. In addition, it would be undesirable and potentially detrimental to the patient if the operating pressure in the dental treatment system was suddenly and unintentionally raised above the selected operating pressure. If such were to occur, the rate of flow and the pressure of the jet stream leaving the dental handpiece would unexpectedly increase beyond the desired pressure range. This unexpected and undesired increase may not only reduce the efficacy of the desired dental treatment, it may also, depending upon the extent of the pressure increase, cause harm and injury to the patient being treated. Accordingly, it is important and highly desirable that the dental treatment systems of the present invention include mechanisms for ensuring that desired pressure is reliably established and that such an unexpected pressure increase does not occur.

An preferred configuration of the downstream portion of pressure selection means 103 is illustrated in FIG. 4. According to the embodiment of FIG. 4 and also indicated in FIG. 1, the system includes means for providing a substantially abrasive-free stream 109 to handpiece 107. Applicant has found that the provision of such means, particularly when such means is operable separately and independently of remaining portions of the pressure selection means, is highly desirable, as described hereinbefore. Accordingly, with reference to FIG. 4, the substantially abrasive-free delivery means comprises, for example, conduit 129 leading from a downstream portion of flow path 116 and selective valve means 131 in the flow path for selectively blocking and unblocking the flow of fluid therethrough. The conduit 129 also contains a pressure regulator 130 to regulate the pressure of the abrasive-free air flowing to the nozzle. Control means 127 is connected to valve means 131 for selectively and independently operating the valve means 131. A check valve 132 and filter 133 are preferably located downstream of valve means 131 for preventing the back flow of fluid or contaminants and abrasives therethrough.

As further illustrated in FIG. 4, the pressure relief means comprises a pressure relief means associated with each selectable pressure range. For example, relief means 134 and 135 are connected to exit manifold means 128 for relieving fluid pressure in the exit manifold to the extent such pressure is in excess of the fluid pressure selected. The exit manifold 128 will, depending upon the operating pressure selected, be subject to at least a relatively high pressure and a relatively low pressure. When the relatively low pressure is selected, no difficulty is presented. On the other hand, the presence of the low pressure relief means in fluid communication with the exit manifold would, in the absence of the pressure relief blocking means of the present invention, prevent operation in the relatively high pressure mode. Accordingly, each pressure relief means 134 and 135 is preferably connected to control means 127 such that the relief means is operative when the pressure range of its associated flow path is selected and inoperative when a higher pressure range is selected. Thus, each pressure relief means 134 and 135 preferably includes a valve means connected to control means 127 for selectively blocking and unblocking flow of pressurized fluid to the respective pressure relief mechanism, depending upon the pressure selected for operating the system. In operation, therefore, the valve means for each relief mechanism is activated to the unblocked position when the operating pressure range associated with that relief means is selected. Conversely, the valve means remains in the unactivated, blocked position when all higher pressure ranges are selected, thus assuring that the desired pressure will be immediately and reliably available to the operator.

C. Control System, Abrasive Delivery and Pressure Relief Means

Figure 5A:
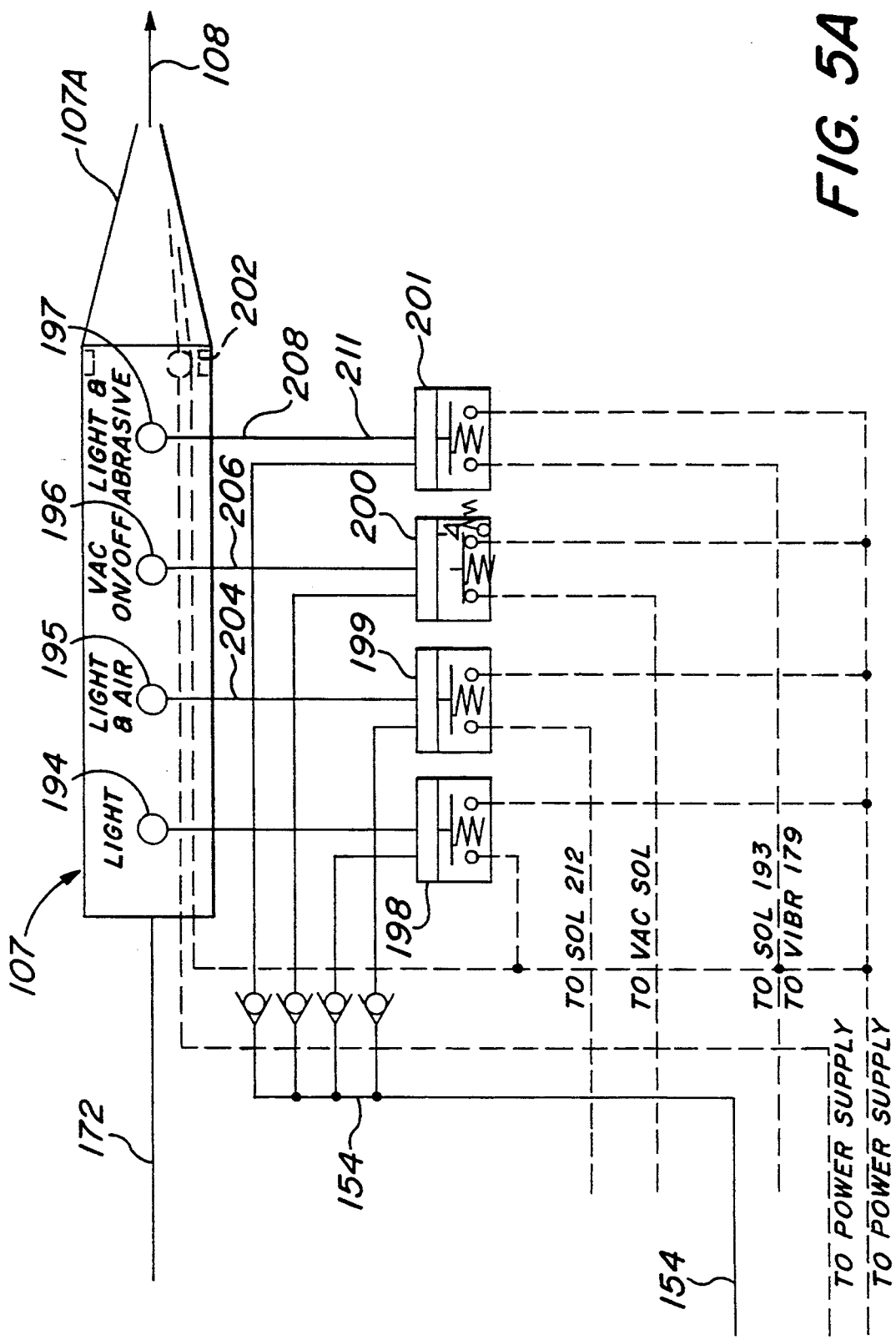

With reference now to FIGS. 5 and 5A, a preferred embodiment showing details of the selective pressure reducing means, including control systems and pressure relief means thereof is disclosed. As fully explained hereinafter, the system illustrated provides for selective delivery of air and abrasive at three discrete pressure levels or a supply of air free of abrasive. Turning first to FIG. 5, the illustrated system includes a source of fluid, preferably air, at a pressure of about 60 to about 90 psig and air supply means 101 which includes means for increasing the pressure of the air so as to supply a stream of air through line 102 at a pressure of from about 80 to about 200 psig. A valve 138 operated by a solenoid 139 is positioned upstream from the supply means 101. Valve 138 is a normally closed valve (hereinafter an NC valve) which is actuated to the opened position by the solenoid 139 upon the closing of a main switch 140. The opening of valve 138 allows the flow of air to a pressure regulator 141 in conduit 123 and to supply means 101 and conduit 102, a check valve 142 to an inlet manifold means comprising the common manifold conduit 143 which corresponds to manifold 20 in FIG. 2 and manifold branch conduits 144 through 146 and the connections therefor.

Each branch conduit 144 through 146 comprises a flow path for the pressurized air and includes therein pressure regulators 148 through 150 for regulating the pressure in a downstream portion of the respective conduit. Although the downstream pressures in conduits 144 through 146 may vary depending upon the particular operations contemplated, it is preferred that they be regulated to a pressure within a high pressure range, a mid pressure range and a low pressure range, respectively. More particularly, a high pressure range of about 160 to 180 psig is preferred for cutting and excavating of tooth enamel, a mid pressure range of about 120 to 140 psig is preferred for etching tooth enamel and a low pressure range of about 80 to 100 psig is preferred for cleaning teeth. In addition, manifold branch line 152, in which a pressure regulator 153 is located, provides for delivery of a supply of regulated air free of abrasives and a manifold branch line 154 in which a regulator 155 is located, provides for delivery of air free of abrasive to the teeth or for the evacuation of abrasive from the system downstream from the abrasive unit, as will be explained hereinafter.

Immediately downstream of the pressure regulators 148 through 150 and 153 are NC valves 148A through 150A operated by solenoids 148B through 150B, respectively. Downstream of the valves 148A through 150A are found check valves 156 through 158, respectively.

Exit manifold means comprising manifold conduit 160 and pressure gauge 161 is connected to and in fluid communication with a downstream portion of each of the conduits 144 through 146. Also connected to and in fluid communication with manifold conduit 160 is a pressure relief means comprising three relief valves 162 through 164 protected by NC valves 166 through 168 operated by solenoids 169 through 171, respectively.

Exit manifold conduit 160 leads from each of conduits 144 through 146 to abrasive delivery means 105 for producing a stream of abrasive-laden gas at the desired pressure to a handpiece 107 through a conduit 172.

From the foregoing, it can be seen that upon closure of main switch 140, NC valve 138 is opened. This allows operatory air to flow through pressure regulator 141 directly to manifold 160 to pressurize the air abrasive delivery system which is preferably of the kind illustrated and claimed in U.S. Pat. No. 4,708,534 and as generally disclosed in FIG. 5B.

The system may further be provided with a switch 101A located in conjunction with the air reservoir within fluid supply means 101. Switch 101A prevents operation of the system, except when there is an adequate pressure level within the reservoir.

Figure 5B:
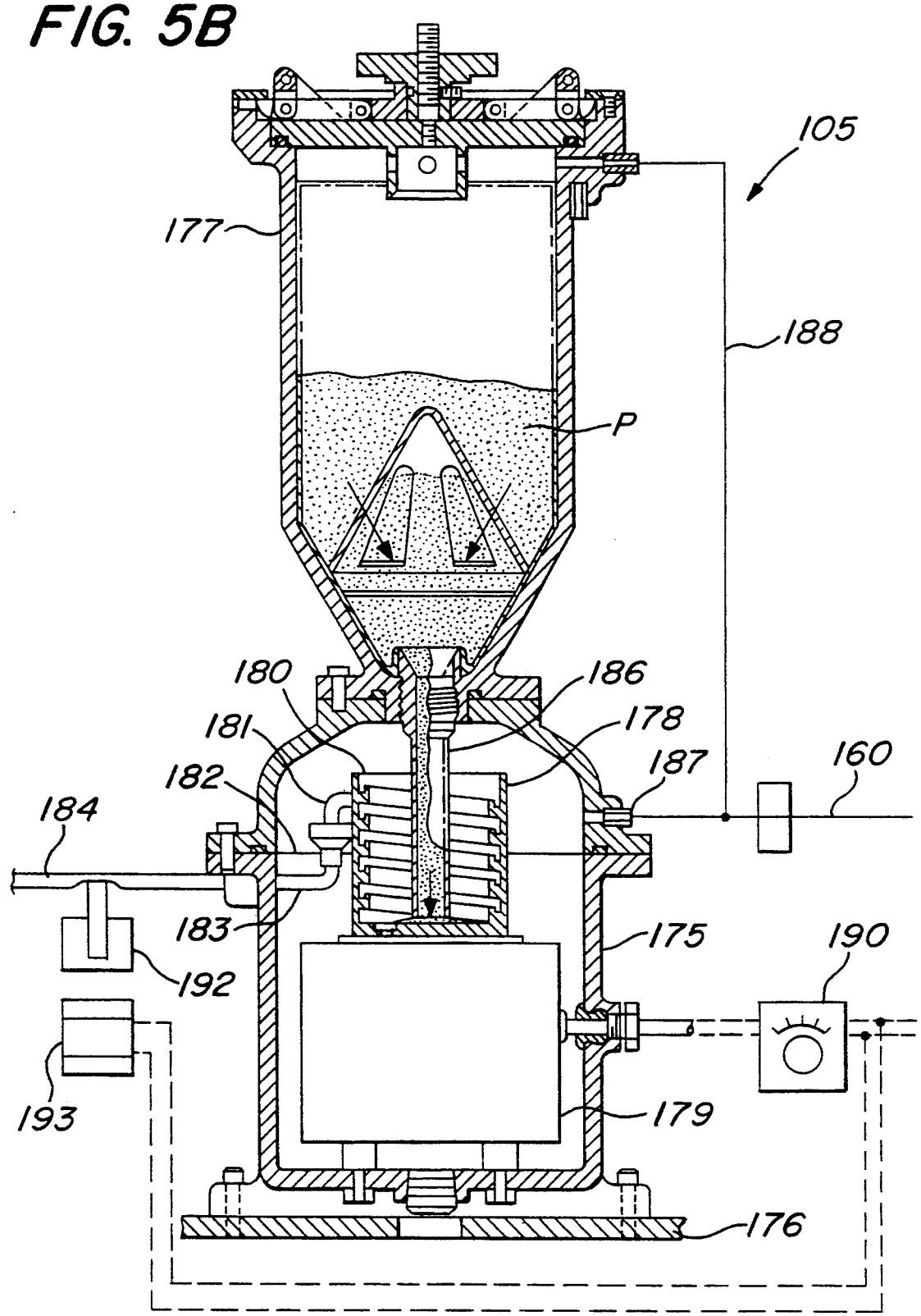
FIG. 5B is a view showing the abrasive delivery system with attendant controls.

With particular reference to FIG. 5B, the preferred form of abrasive delivery system 105 will be described briefly. The system includes a sealed lower chamber 175 mounted on a base 176 and an abrasive powder supply vessel 177 which is bolted or otherwise fastened to the top of chamber 175. Located within chamber 175 is an upwardly open cylindrical particle feed receptacle 178 which is mounted on a vibratory device 179, as particularly described in the aforesaid U.S. Pat. No. 4,708,534. Cylindrical feed receptacle 178 is provided on its inner surface with a helical feed groove 180, the lower end of which communicates with the bottom of the cylinder and the top of which is in communication with a feed tube 181 which delivers the particulate material through a section of resilient, flexible tubing 182 to an exit tube 183 which passes through the wall of vessel 175. Joined to tube 183 is a second section of resilient flexible tubing 184 which is in turn connected to a duct 172 which leads to handpiece 107, as is illustrated in FIG. 5.

Powder supply receptacle 177 is adapted to receive and contain a supply of particulate abrasive matter, generally indicated by the reference character P and to supply the same in a uniform manner to the bottom of cylindrical feed device 178 through a feed tube 186 in a manner more particularly described in U.S. Pat. No. 4,708,534.

In order to bring the powder delivery system up to a pressure at which it is primed for operation, air under pressure, for example, of about 80 psi, is delivered to chamber 175 by way of a connection 187 which is connected to line 160 which is pressurized upon closure of valve 138 when main control switch 140 is closed. A branch conduit 188 also supplies air at the same pressure to the powder supply chamber 177 by means of a connection 189 which communicates with the interior of the supply chamber 177.

Vibratory device 179 is an electrically operated device which is preferably activated off handpiece 107 by means to be described hereinafter. In general, the rate of vibratory feed is controlled by way of a preset adjustable control device 190 mounted on the equipment control panel in a convenient location. Device 190 may be set manually by the operator to a desired vibratory rate or optionally may be a pressure responsive device which automatically adjusts through connections to switch 191 so that an appropriate rate is provided for the operating pressure level as selected on switch 191.

The abrasive delivery system is also preferably provided with a normally closed valve 192 which is preferably a pinch valve of the kind illustrated more particularly in FIG. 10 of the aforesaid U.S. Pat. No. 4,708,534. Pinch valve 192 is controlled by a solenoid 193 either directly or through a fluid pressure device. The solenoid 193 is preferably energized upon closure of a switch activated off the handpiece to maintain pinch valve 192 in the open position whenever vibrator 179 is in operation.

In summary, when the main switch 140 is closed, chambers 175 and 177 are immediately pressurized at the low end of the operating pressure range so that the abrasive delivery system is readied for the delivery of a particulate-laden air stream through resilient tube 184 to conduit 185 when desired by the operator. Upon activation of the vibrator and opening of pinch valve 192 by the control circuitry, described hereinafter, particulate material advances upwardly within spiral groove 180 through duct 181 where it enters resilient, flexible tubing 182 and exit tube 183, where it exits container 175 and passes through tube 184 to join conduit 185.

It will be appreciated by those skilled in the art that it may be desirable to use different abrasives and/or different particle size abrasives for different dental operations. For example, it may be desirable to utilize abrasive particles having one set of characteristics for a first dental operation and a second set of characteristics for a second dental operation. While it is possible to manually change the type of abrasive being used, it is preferred that the abrasive delivery system of the present invention include means for selectively providing either a first abrasive particle or a second abrasive particle for mixing with the fluid stream. One apparatus capable of achieving this result is disclosed in U.S. Pat. No. 2,661,537 to Angell, which is incorporated herein by reference.

As explained above, closure of main switch 140 also allows the operatory air to be delivered to the air pressure intensifier 101 which preferably increases the pressure of the available air to be supplied to a level of approximately 200 psig. Air at this pressure is then delivered through conduit 143.

FIG. 5 further illustrates the system provided for controlling the selective pressure reduction means and for selective delivery to the handpiece of pure air under pressure or a pressurized air and abrasive mix as required. The control system preferably involves the use of separate pressure selector switch 191 and additionally includes controls on the dental handpiece 107, operation of the selective pressure reduction means being described first.

The pressure selector switch 191 is located in any convenient position on the control panel or optionally and/or additionally may be incorporated in a foot actuated switching device of a type well known in the art. As is illustrated in FIG. 5, when switch 191 is in the open position (as shown), the NC valves 148A through 150A remain closed and the flow of operating fluid through any one of valves 148A through 150A is thus blocked.

With switch 191 in any one of the closed positions, the appropriate solenoid 148B through 150B is energized, thereby allowing fluid to flow through the appropriate conduit 144 through 146. As seen in FIGS. 5 and 5A, conduit 144 through 146 deliver air to manifold 160 at a pressure established by the respective pressure regulator 148 through 150.

Since the pressure in conduit 160 can be within any one of the three above described pressure ranges, the pressure relief means includes first, second and third relief valves for relieving pressure in excess of said first, second and third pressure ranges, respectively. The first relief valve 162 is calibrated with an activation pressure which corresponds to or is slightly greater than the maximum operating pressure in the downstream portion of flow path 144, while relief valves 163 and 164 are calibrated to have activation pressures which correspond to or are slightly greater than the maximum operating pressure in the downstream portions of flow paths 145 and 146, respectively. When a control signal is transmitted to solenoid 148 to open valve 148A, solenoid 169 is activated by the same control signal, thereby opening blocking valve means 166. However, blocking valves 167 and 168 remain closed, thereby isolating the relief valves 163 and 164 from the operating fluid when the system is operated in the high pressure mode. It will be understood that similar operation occurs in the mid- or low-pressure modes.

As indicated above, means are provided to deliver air at relatively low pressure as established by pressure regulator 153 through the conduit 152. This conduit bypasses the abrasive supply unit 105, delivering a regulated supply of air at a relatively low pressure directly to the inlet of the handpiece 107 to provide the operator with a stream of abrasive-free air useful for drying the region of the tooth as is frequently desired. For this purpose, normally closed valve 151A in line 152 is opened by energization of a solenoid 151B which is preferably controlled by a pressure operated switch activated by closure of one of a group of control ports on handpiece 107, as described below. Line 152 is further provided with a filter 152A and check valve 159 to isolate the valve components from the air and abrasive mixture.

In one condition of operation of the system, as will be described subsequently, the air delivered through line 152 may also be used to create a vacuum downstream from the abrasive delivery system so as to effect removal of the mixture of abrasive and/or debris from the interior of the handpiece.

As indicated just above, a plurality of control ports provided on the handpiece 107 enable certain functions of the system of the present invention. According to the preferred embodiment of the invention, shown in FIG. 5, the handpiece is preferably provided with four fluid control ports 194 through 197, each of which is conveniently located to be closed by a finger of the operator. Ports 194 through 197 are located in series-circuit relationship with a relatively low pressure supply of air, supplied for example, through branching conduit 154 and regulated by pressure regulator 155 (FIG. 5). The ports 194 through 197 control three normally open diaphragm operated pressure switches 198, 199 and 201 and one diaphragm operated latching switch 200, each of which receives pressurized air from conduit 154. So long as handpiece ports 194 through 197 are uncovered, air at a relatively low pressure passes through the diaphragm chamber of each of the switches 198 through 201 and exits through the ports. However, upon closure of a selected one of ports 194, 195 and 197, one or more of the normally open switches 198, 199 and 201 will be closed on account of the increase in pressure to which the diaphragm in the switch is subjected. In the case of latching switch 200, momentary closure of port 196 is effective to latch switch 200 in the closed position if initially opened and to return it to the open position if closed.

As illustrated in FIG. 5A, port 194 is a lamp activation port which communicates with the diaphragm chamber of switch 198 which, when closed, energizes a circuit which lights a lamp 202 (which may include a fiber optic device) which casts a beam of light through an opening in the distal end of handpiece 107 for the purpose of illuminating the area of a tooth or related tooth structure being worked on by the operator. So long as port 194 is closed, the lamp 202 remains illuminated.

Port 195 is a light and air activation port which is in communication with normally open lamp switch 198 through a conduit 204 and 205 and in communication with the diaphragm chamber of normally open diaphragm operated switch 198 by means of conduits 204 and 205 so as to effect closure of switches 198 and 199 when port 195 is closed, thus turning on lamp 202 and activating solenoid 212 so as to close valve 213 to deliver air free of abrasive from conduit 152 to the handpiece.

Port 196 is a powder evacuation activator port which is in communication with latching switch 200 by means of conduit 206 and may also be in communication with the light switch 199 by means of a branch conduit 207. Upon closure of port 196, the light will be turned on and switch 200 closed to energize a solenoid 191A which activates switch 191 to turn on vacuum 221, as described hereinafter in reference of FIG. 6.

Port 197 is the port for activation of the powder delivery system and is in communication with normally open diaphragm operated switch 201 via lines 208 and 211. Closure of switch 201 by placing a finger over port 197 energizes solenoid 193 to open pinch valve 192 and turns on vibrator 179. Simultaneously, solenoid 212 is energized to close normally opened purge valve 213. The relatively high pressure air abrasive mixture is directed through conduit 172 and out through nozzle 107A. Since the pressure of the air and abrasive mix is high relative to the pressure of the air in line 152, check valve 159 blocks flow of pure air through line 152. However, as soon as the user removes his finger from port 197 to terminate the delivery of the air and abrasive mix, pure air again flows past the check valve 159. Opening of the switch deenergizes solenoid 212 to open pinch valve 214 so that air flows out through purge line 214. Because there is a small orifice in the tip of handpiece 107 relative to the cross-section of the purge line, the rush of air creates a vacuum.

As indicated in FIGS. 5 and 5A, the various branch circuits are provided with check valves to insure that closure of a particular port activates only through switches which are required to perform the functions indicated. In addition, filters 152A and 217 provided in lines 152 and 160 insure that abrasive does not enter the manifold system.

Although the use of the above-described fluid ports constitute a preferred method of control, it should be understood that electrically operated switches positioned on the handpiece and utilizing a low voltage power source could be employed without departing from the scope of the invention.

D. Dental Handpiece Means

It will be appreciated by those skilled in the art that the particular form of the handpiece 107 may vary widely, depending upon factors such as cost and portability. In general, it is preferred that the handpiece be adapted to be carried and manipulated by the dentist or other dental professional. For this reason, handpiece 107 is generally formed in the shape of an elongate cylinder connected to the abrasive/fluid delivery means 105 by way of the conduit 172 (see FIG. 5), which conduit should be flexible for ease of manipulation. A central bore in the handpiece transports the abrasive-laden fluid to a nozzle means 107A disposed at the distal end thereof.

In addition, the handpiece is provided with a fiber optic channel to accommodate lamp 202 and a fiber optic device which terminates at the distal end of portion 107A for the purpose of directing light in the area of impact of the abrasive particles. The nozzle means 107A may be, for example, frusto-conically shaped, thereby providing a cross-sectional flow area which reduces gradually from that of about the central bore to a relatively small opening in the end of the nozzle. This reduction in flow area results in a concomitant increase in fluid velocity, thereby producing a stream or jet of abrasive-laden fluid 108 which is effective for cutting, etching or cleaning teeth or related tooth structure, depending upon the operating pressure of the system. The particular configuration and construction of such handpieces is generally well known, and all such constructions are within the scope of the present invention. One such handpiece is shown in U.S. Pat. No. 2,696,049, which is incorporated herein by reference. As illustrated in the '049 patent, the nozzle portion of the delivery means is preferably readily removably attached to the handpiece. Such removability is beneficial in several respects. First, it will be appreciated that the flow of high velocity abrasives through the nozzle 107A of the present dental treatment systems will tend to cause wear and abrasion of the internal channel of the nozzle. This could, in turn, reduce the efficacy of the system. Accordingly, the provision of a removable nozzle permits replacement of the nozzle as needed to maintain the efficacy of the system. In addition, applicant contemplates that the nozzle 107A may, in certain embodiments, be comprised of a relatively inexpensive material, such as plastic. In such embodiments, it is expected that the nozzle would be discarded after each use. The provision of such a low cost, inexpensive replaceable nozzle has the obvious advantage of reducing a likelihood of the spread of infectious disease from one patient to the next. It is contemplated that the removability of the present nozzle may be achieved by providing the nozzle with a threaded portion, as disclosed in the '049 patent, or other means, such as providing a bayonet type attachment between the nozzle and the remainder of the handle portion. In addition, the entire handpiece should be separable from conduit 172 and from its associated control lines to permit autoclaving.

According to another preferred embodiment of the present invention, the portion of the nozzle which comes in contact with the abrasive-laden fluid stream may be formed of a hard, abrasion-resistant material, such as carbide. Thus, the nozzle itself can be formed of such carbide material, or formed of less expensive materials which are lined with carbide or similar abrasion-resistant materials.

E. System for Evacuating Abrasive Material

Figure 6:
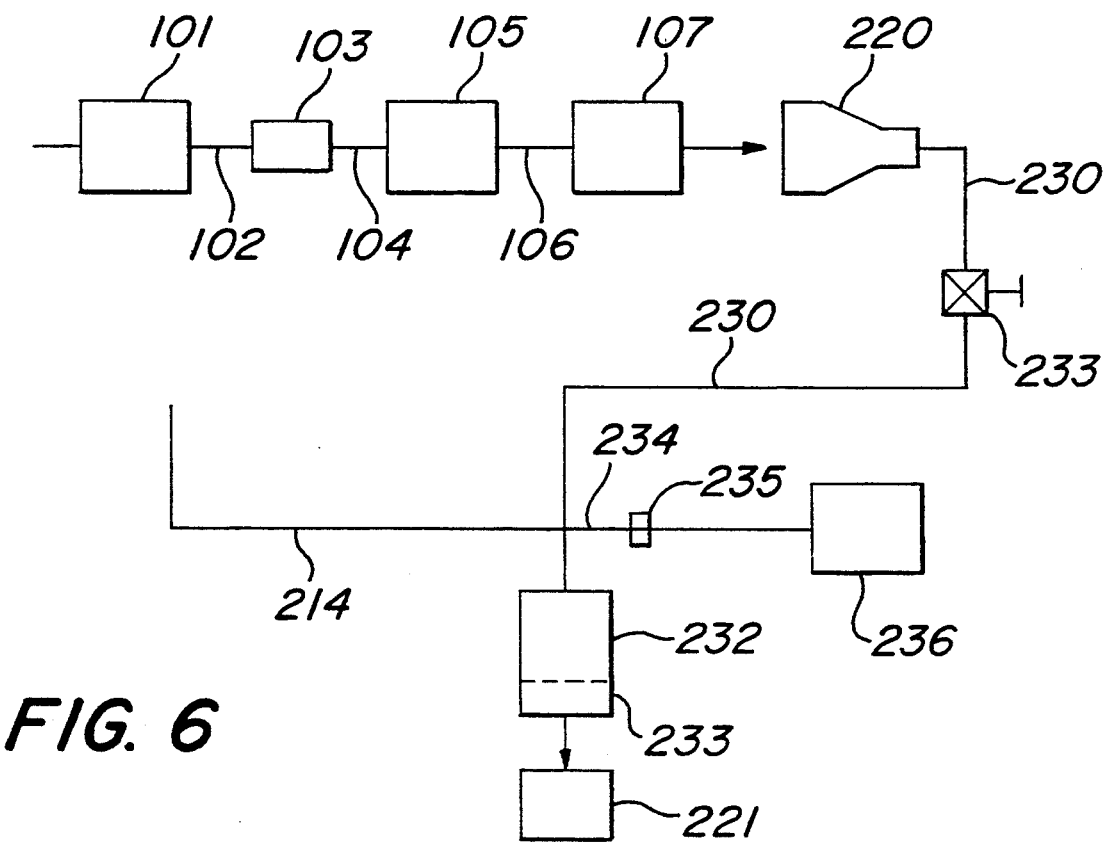
FIG. 6 is a block diagram illustrating one embodiment of the treatment system of the present invention in combination with one embodiment of the evacuation system of the present invention.
Figure 6A:
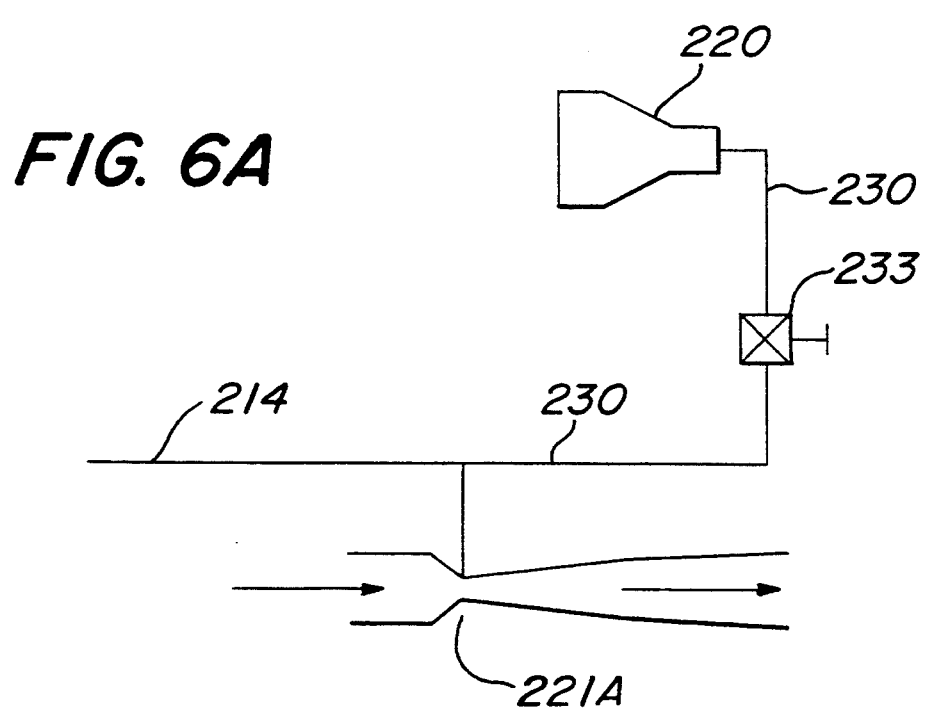
FIG. 6A is a block diagram illustrating a second embodiment of an evacuation system of the present invention.
Figure 7:
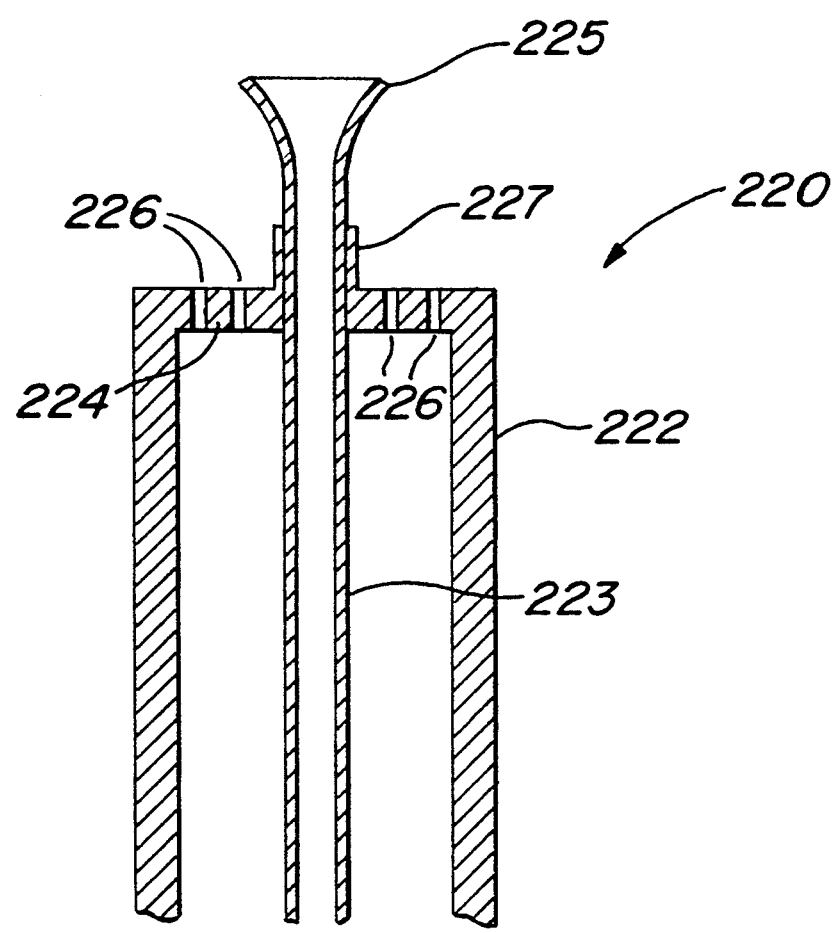
FIG. 7 is a cross-sectional view of a two-stage evacuation nozzle according to one embodiment of the present invention.

In its preferred form, the dental treatment system of the present invention includes the provision of means for effectively and efficiently evacuating excess abrasive particles from the area of the mouth after treatment. As noted, above, the failure of prior art dental treatment systems to effectively deal with the continued removal of abrasive particles from the mouth has contributed to the lack of acceptance of the systems. With particular reference to FIGS. 6, 6A and 7, the invention preferably includes a two-piece vacuum nozzle means, generally indicated at 220, adapted to be placed in the mouth of a patient and a means for creating a vacuum within the nozzle means so as to draw away the abrasive particles and debris.

According to FIG. 7, nozzle means 220 preferably includes an outer tubular housing section 222 and an inner tubular section 223 co-axially mounted within section 222 by means such as a support plate 224. Preferably, inner tubular member 223 has an outwardly flared portion 225 which is intended to be positioned adjacent to the region of the patient's mouth during treatment. A plurality of spaced apart openings 226 are located in a plate 224.

Preferably, inner tubular conduit section 223 is frictionally fitted within a sleeve or collar 227 which is joined to support plate 224. The frictionally interfitting portions provide a means permitting longitudinal adjustment of inner tubular member relative to the outer section 222 so as to permit movement of the flared portion 225 to accommodate patients having different sized mouths and/or to allow for adjustment to bring the flare portion into different areas of the mouth.

Evacuator nozzle 220 is connected to a flexible hose 230 which is coupled onto the end of the outer tubular housing section 222. Preferably, the cross-sectional area of the openings 226 and the cross-sectional area of the inner tubular section 223 should roughly equal the cross-sectional area of tube 230 so as to avoid an unwanted choking down of the air drawn from the patient's mouth. As indicated in FIG. 6, conduit 230 preferably is connected to the vacuum means 221 which comprises a conventional electric motor operated vacuum system which, in one embodiment, includes a rigid, removable disposable container 232 within which the used abrasive and debris is collected. A valve 233 within conduit 230 blocks flow through the conduit. As indicated in FIG. 6, valve 233 is manually operated. In addition, pressure selector switch 191 operates electric motor for vacuum 221 so as to draw air from the nozzle 107A and the patient's mouth area as soon as a particular pressure is selected, thereby avoiding the possibility of excess abrasive escaping to the atmosphere. With the system described, substantially all abrasive delivered to the patient's mouth, as well as the debris created by the cleaning, abrading and cutting operations, is captured by the vacuum system and delivered to the rigid disposable container 232 which is preferably readily sealable for separate handling and disposable at a medical disposal waste site, if necessary.

FIG. 6 also illustrates purge line 214 which, as explained above, is opened so as to convey away abrasive from the system downstream from the air abrasive means 105 when the operator removes his finger from handpiece port 197. Desirably, a filter 233 filters out any abrasive drawn through conduits 230 or 214 by vacuum means 221.

FIG. 6A illustrates an alternative form of means for creating a vacuum. According to FIG. 6A, the vacuum means comprises a water venturi shown at 221. Both conduits 214 and 230 are connected to the throat of the venturi. The flow of water through the venturi creates a subatmospheric pressure in the throat drawing excess abrasive from evacuator nozzle 220 and purge line 214.

With reference back to FIG. 6, the system may also comprise a branch passage 234 which has a connector 235 which permits connection to the standard suction system 236 available in most dental offices.

The operation of the illustrative embodiment of the invention will now be briefly summarized with particular reference to FIGS. 5A and 5B.

When main power switch 140 is turned on, solenoid 139 effects the opening of valve 138 delivering air under pressure of between about 60 and 90 psig to the pressure intensifier 101. Simultaneously, a regulated supply of air is delivered through conduits 123 and 160 to the air abrasive delivery unit priming this unit by pressurizing chamber 175 and powder supply 177.

The operator chooses the particular operating pressure for delivery of the air-abrasive mixture through use of selector switch 191 which may be conveniently located on the instrument panel or, alternatively, through a four-position foot activated switch, not shown, having four actuating positions which are connected in parallel with the contacts of switch 191.

At this point, the device is fully primed for operation which is achieved through selective control by closure of an appropriate port on the dental handpiece 107. If the operator wishes to only illuminate the tooth or related tooth structure to be worked on, he closes finger port 194 which effects closure of the lamp circuit to light lamp 202. If the operator then wishes to direct a jet of drying air to the tooth or tooth structure, finger port 195 is closed which effects energization of the lamp circuit and a closure of purge valve 213.

Closure of port 196 latches switch 200 in the closed position which activates the vacuum system of FIG. 6. Finally, when the operator is ready to apply the air abrasive mix to the tooth or tooth region, the covers port 197 which energizes solenoid 193 to open pinch valve 192, turns on vibrator 179 and closes normally open purge valve 213. When port 197 uncovered, the flow of air and abrasives stops, the purge valve 213 is opened and air through line 152 purges portions of the system downstream of abrasive unit 105 of abrasive materials.

In the illustrative embodiment, the vacuum system is activated whenever pressure selection switch 191 is turned on with the result that abrasive particles and tooth debris are drawn from the region of the patient's mouth whenever an air/abrasive mixture is delivered by the handpiece as well as when drying air alone is delivered and when the operator is merely inspecting the area being treated.

Through the unique combination of pressure relief valves 162 through 164 and blocking valves 166 through 168, the pressure chosen for use in the treatment of teeth may be readily and rapidly changed by use of selector switch 191. When switching from a higher to a lower operating pressure, the change occurs immediately, enabling the operator to work confidently and without delay. Still further, switch over from cutting and abrading to the use of air only for cleaning and drying the tooth region being worked on or the use of the light only can be readily and rapidly accomplished by controls conveniently located on the dental handpiece.

What is claimed is:

1. A system for performing a dental procedure on teeth or associated tooth structure by means of abrasive particles carried by a fluid stream comprising, in combination with a source of fluid;
   (a) means for increasing the pressure of said fluid to about an initial pressure;
   (b) pressure selection means for selectively providing said fluid at at least a first pressure or a second pressure, each of said first and second pressures being less than about said initial pressure;
   (c) abrasive mixing means for combining the abrasive particles with said fluid at either said first pressure or said second pressure to provide an abrasive-laden fluid stream;
   (d) selectively operable means for activating and deactivating said abrasive mixing means;
   (e) nozzle means for delivering said abrasive-laden fluid stream to the teeth or tooth structure undergoing said dental procedure; and
   (f) means for evacuating excess abrasive materials, post-use abrasive materials and other debris from the area of the mouth of the patient being treated, said evacuation means including means in juxtaposition to the mouth of the patient for creating a negative pressure in the mouth region effective to withdraw abrasive materials and debris from the mouth.

2. A system according to claim 1, wherein said means for creating a negative pressure further comprises a collection device adapted to be placed adjacent the patient's mouth, a conduit leading from said collection device, said conduit including a connection means for connection of said conduit to the dental office suction system.

3. A system according to claim 1, wherein said evacuation means further includes a rigid substantially closed abrasive collection container for collection of said abrasive materials and other debris.

4. A system according to claim 1, further including a purge conduit means intermediate said abrasive mixing means and said nozzle means, means for activating said purge conduit means to effect removal of abrasive particles from said system downstream of said abrasive mixing means when said abrasive mixing means is deactivated, said purge conduit means and said evacuation means having a common connection to a source of negative pressure.

5. A system according to claim 4, further including an abrasive and debris removing filter common to said purge conduit means and said evacuation means.

6. A system according to claim 4, wherein said source of negative pressure comprises means for connection to the dental office suction means.

7. A system according to claim 4, wherein said source of negative pressure comprises a sealable, disposable abrasive collection container, a vacuum device for drawing abrasive materials and debris into said container and a common filter between said collection container and said vacuum device.

8. Apparatus according to claim 1, wherein said means for creating a negative pressure comprises a water venturi, means for circulating a stream of water through the low pressure region of said venturi and a negative pressure conduit extending from the low pressure region of the venturi and said means in juxtaposition to the mouth of the patient, whereby abrasive materials and debris are withdrawn into the stream of water circulating through said venturi.

9. A system for the practice of a dental procedure on teeth or associated tooth structure by the use of an abrasive-laden fluid stream comprising, in combination with a source of pressurized fluid:
 (a) manifold means connected to said source of pressurized fluid for providing at least first and second parallel flow paths for said pressurized fluid;
 (b) first pressure reducing means in said first flow path for providing said fluid at a first pressure in a downstream portion of said flow path, said first pressure being less than about said initial pressure;
 (c) second pressure reducing means for providing said fluid at a second pressure in a downstream portion of said second flow path, said second pressure being less than about said first pressure;
 (d) second manifold means for combining said first and second flow paths;
 (e) blocking means for selectively blocking or unblocking fluid communication between said second manifold means and said downstream portion of said second flow path;
 (f) abrasive mixing means for combining pressurized fluid from said second manifold means with the abrasive material to produce a pressurized stream of abrasive-laden fluid;
 (g) delivery means for delivering said stream of abrasive-laden fluid to the teeth or tooth structure undergoing said dental procedure;
 (h) an abrasive evacuation means, including a negative pressure device positioned in juxtaposition to the mouth of the patient for evacuation of abrasives and tooth debris, said evacuation means including a rigid, sealable and removable disposable abrasive collection container for disposal of said abrasive and said debris;
 (i) a purge conduit means in communication with said nozzle means and said fourth flow path, said purge conduit means including a purge valve selectively operable and control means for activating said purge valve for direction of fluid from said fourth flow path and said nozzle means through said purge valve, activation of said purge valve effecting removal of abrasive particles from portions of said system downstream from said abrasive mixing means; and
 (j) means interconnecting said purge conduit means with said disposable abrasive collection container.

10. A system according to claim 9, further including a vacuum device for drawing abrasive into said disposable abrasive collection container and a common abrasive particle and debris removing filter for fluid drawn through said purge conduit means and from said evacuation means.

11. A system for the practice of a dental procedure on teeth or associated tooth structure by the use of an abrasive-laden fluid stream comprising, in combination with a source of pressurized fluid:
 (a) manifold means connected to said source of pressurized fluid for providing at least first and second parallel flow paths for said pressurized fluid;
 (b) first pressure reducing means in said first flow path for providing said fluid at a first pressure in a downstream portion of said flow path, said first pressure being less than about said initial pressure;
 (c) second pressure reducing means for providing said fluid at a second pressure in a downstream portion of said second flow path, said second pressure being less than about said first pressure;
 (d) second manifold means for combining said first and second flow paths;
 (e) blocking means for selectively blocking or unblocking fluid communication between said second manifold means and said downstream portion of said second flow path;
 (f) abrasive mixing means for combining pressurized fluid from said second manifold means with the abrasive material to produce a pressurized stream of abrasive-laden fluid;
 (g) delivery means for delivering said stream of abrasive-laden fluid to the teeth or tooth structure undergoing said dental procedure;
 (h) an abrasive evacuation means, including a negative pressure device positioned in juxtaposition to the mouth of the patient for evacuation of abrasives and tooth debris, said evacuation means including a rigid, sealable and removable disposable abrasive collection container for disposal of said abrasive and said debris;
 (i) a purge conduit means in communication with said nozzle means and said fourth flow path, said purge conduit means including a purge valve and control means for opening said purge valve for direction of fluid from said fourth flow path and said nozzle means through said valve, opening of said purge valve effecting removal of abrasive particles from portions of said system downstream from said abrasive mixing means;
 (j) means interconnecting said purge conduit means with said disposable abrasive collection container;
 (k) an abrasive evacuation means including a collection device positioned adjacent the mouth of the patient for evacuation of abrasives and tooth debris; and
 (l) means for connection of said collection device to a source of negative pressure.

12. A system according to claim 11, wherein said source of negative pressure comprises a water venturi device, means for circulation of a stream of water through said venturi device whereby a zone of negative pressure is established and a negative pressure fluid line interconnecting said negative pressure zone and said abrasive evacuation means for withdrawal of said abrasive and said tooth debris into the stream of water circulating through said venturi.

13. A system according to claim 12, further including means establishing a fluid connection between said purge conduit means and said negative pressure fluid line.

14. A system according to claim 11, wherein said source of negative pressure is the dental office suction system.

* * * * *

UNITED STATES PATENT AND TRADEMARK OFFICE
CERTIFICATE OF CORRECTION

PATENT NO. : 5,350,299

DATED : September 27, 1994

INVENTOR(S) : Gallant

It is certified that error appears in the above-identified patent and that said Letters Patent is hereby corrected as shown below:

Column 1, line 35, insert --of-- after "use"

Column 3, line 18, change " - " to --.--

Column 4, line 1, delete " - ", second occurrance

Column 8, line 18, delete "a"

Column 9, line 34, change "An" to --A--

Column 15, line 64, insert -- - -- after "bayonet"

Column 16, line 14, after "noted" delete ","

Column 17, line 49, change "the covers" to --he covers--

Signed and Sealed this

Ninth Day of May, 1995

Attest:

Attesting Officer

BRUCE LEHMAN

Commissioner of Patents and Trademarks